United States Patent [19]
Hung et al.

[11] Patent Number: 5,643,579
[45] Date of Patent: Jul. 1, 1997

[54] ORAL VACCINES

[75] Inventors: Paul P. Hung, Bryn Mawr; Alan R. Davis, Wayne, both of Pa.

[73] Assignee: American Home Products Corporation, Madison, N.J.

[21] Appl. No.: 283,231

[22] Filed: Jul. 29, 1994

Related U.S. Application Data

[63] Continuation-in-part of Ser. No. 805,121, Dec. 11, 1991, abandoned, which is a continuation-in-part of Ser. No. 426,336, Oct. 24, 1989, abandoned, which is a continuation-in-part of Ser. No. 58,002, Jun. 4, 1987, Pat. No. 4,920,209, which is a continuation-in-part of Ser. No. 782,638, Oct. 4, 1985, abandoned, which is a continuation-in-part of Ser. No. 667,233, Nov. 1, 1984, abandoned.

[51] Int. Cl.$^6$ .................... A61K 39/29; A61K 39/12; A61K 39/23; C12P 21/06
[52] U.S. Cl. .................... 424/227.1; 424/205.1; 424/218.1; 424/189.1; 424/233.1; 435/69.1
[58] Field of Search .................... 424/205.1, 184.1, 424/208.1, 218.1, 233.1, 204.1, 189.1, 227.1

[56] References Cited

FOREIGN PATENT DOCUMENTS

WO8302393 of 1983 WIPO.

OTHER PUBLICATIONS

Chanock et al., JAMA, 195, 151 (1967).
Edman et al., Nature, 291, 503 (1981).
Valenzuela et al., Nature, 298, 347 (1982).
Miyanohara et al., Proc. Natl. Acad. Sci USA, 80, 1 (1983).
Smith et al., Nature, 302, 490 (1983).
Kalica et al., Virology, 112, 385 (1981).
Richardson et al., J. Virol. 51, 860 (1984).
Solnick, D., Cell 24, 135 (1981).
Thummel et al., Cell 23, 825 (1981).
Gluzman, Y., Eukaryotic Viral Vectors, Cold Sp. Harbor, p. 187 (1982).
Rigby et al., J. Gen. Virol, 64, 255 (1983).
Elleman et al., Nucleic Acids Res. 11, 4689 (1983).
Kitchingman, Gene, 20, 205 (1982).
Davis, et al, 1985, "Expression of hepatitis B . . . " PNAS 82:7560–7564.
Hung, et al, 1988, "Adenovirus as the carrier . . . " Tech. Advances in Vacine Dev. : 267–277.
Richardson, et al, 1984, "Nucleotide sequence of the gene . . . " J. Virol. 51(3) : 860–862.
Lubeck, et al, 1989, "Immunogenicity and efficacy testing . . . " PNAS 86 : 6763–6767.
Morin, et al, 1987, "Recombinant adenovirus induces antibody . . . " PNAS 84: 4626–4630.
*Virology*, Ginsberg, "Reoviruses and Epidemic Acute Gastroenteritis Viruses": Rotaviruses, pp. 315–318, 1988.

*Primary Examiner*—Lynette F. Smith
*Attorney, Agent, or Firm*—Steven R. Eck

[57] ABSTRACT

Methods and vaccines for the production of antibodies to infectious organisms are described. Live recombinant adenovirus containing a foreign gene coding for an antigen produced by another infectious organism is delivered to the intestine of a warm-blooded animal in an enteric-coated dosage form, whereupon the virus infects the gut wall and induces the production of antibodies or cell mediated immunity to both adenovirus and the other infectious organism.

54 Claims, No Drawings

ORAL VACCINES

This application is a continuation-in-part of co-pending U.S. Ser. No. 07/805,121, filed Dec. 11, 1991 now abandoned, which is a continuation-in-part of U.S. Ser. No. 07/426,336, filed Oct. 24, 1989, now abandoned, which is a continuation-in-part of U.S. Ser. No. 07/58,002, filed Jun. 4, 1987, now U.S. Pat. No. 4,920,209, which is a continuation-in-part of U.S. Ser. No. 06/782,638, filed Oct. 4, 1985, now abandoned, which is a continuation-in-part of U.S. Ser. No. 06/667,233, filed Nov. 1, 1984, now abandoned.

BACKGROUND OF THE INVENTION

A major goal of biomedical research is to provide protection against viral disease through immunization. One approach has been to use killed vaccines. However, large quantities of material are required for killed vaccine in order to retain sufficient antigenic mass. In addition, killed vaccines are often contaminated with undesirable products during their preparation. Heterologous live vaccines, using appropriately engineered adenovirus, which is itself a vaccine, Chanock R. M. et al., JAMA, 195, 151 (1967), seem an excellent immunogen. Our invention concerns live oral vaccines using adenovirus as vector.

Presently marketed adenovaccine comprises live, infectious adenoviruses in an enteric-coated dosage form. Upon administration to the patient to be vaccinated, the virus is carried past the upper-respiratory system (where disease-producing infection is thought to occur), and is released in the intestine. In the intestine, the virus reproduces in the gut wall, where, although it is not capable of causing adenoviral disease, nevertheless induces the formation of adenovirus antibodies, thus conferring immunity to adenoviral disease. In our invention, live, infectious adenovirus which has been engineered to contain genes coding for antigens produced by other disease-causing organisms is administered in an enteric-coated dosage form. Upon release in the intestine the virus will reproduce in the gut wall, will separately express both the adenoviral antigen and the pathogen surface antigen, and will induce the formation of antibodies or induce cell mediated immunity to both adenovirus and the other disease-causing organism. By "live virus" is meant, in contradistinction to "killed" virus, a virus which is, either by itself or in conjunction with additional genetic material, capable of producing identical progeny. By "infectious" is meant having the capability to deliver the viral genome into cells.

Approximately 200,000 persons in the United States are infected each year with Hepatitis B virus. In addition, there is a strong correlation between hepatitis B infection and liver cancer. The presently marketed vaccines against hepatitis B are injectable products containing hepatitis antigen obtained from the blood plasma of healthy carriers or from expression by recombinant microorganisms.

There are two major hepatitis B viral antigens: the surface antigen ($HB_sA_g$) and the core antigen ($HB_cA_g$). The antigenic structure of $HB_sA_g$ is somewhat complex. There is a common group-specific determinant, a. In addition, there are two sets of mutually exclusive type-specific determinants d or y and w or r. The $HB_cA_g$ is of a single antigenic type. It is known that production of antibody against $HB_sA_g$ or $HB_cA_g$ confers immunity against hepatitis B infection.

Several groups have employed recombinant DNA techniques to synthesize the $HB_sA_g$ by microorganisms. $HB_sA_g$ has been synthesized in *Escherichia coli* in the form of a fusion protein (Edman, J. C. et al., Nature, 291, 503 (1981)). It has also been synthesized in yeast using the ADH promoter (Valenzuela et al., Nature 298, 347 (1982)) or acid phosphatase promoter (Miyanohara et al., Proc. Natl. Acad. Sci. USA, 80, 1 (1983)). The expression of $HB_sA_g$ by Adenovirus in eukaryotic cell strains has also been proposed (Rutter et at., European Patent Publication 62,574 (1982), and described (Perricaudet, et al., European Patent Publication 185,573 (1986)), as has the possibility of using adenoviruses modified at the E3 region by the insertion of recombinant DNA in the constitution of live vaccines, Bailay et al., EMBO Journ. 4, 3861 (1985). Saito et al. describe the construction of an adenovirus containing hepatitis B viral DNA (J. Virol. 54, 711 1985). Vaccinia virus has been used as a vector to produce a live virus vaccine to hepatitis virus (Smith et al., Nature, 302, 490 (1983)).

Rotaviruses are a major cause of acute gastroenteritis in infants. These viruses possess a genome of eleven double-stranded RNA segments enclosed in a capsid. The capsid contains an inner and outer shell. One of the outer shell proteins, VP7, is a glycoprotein that reacts with serotype-specific neutralizing antibodies (Kalica, A. R. et al., Virology, 112, 385 (1981)). This protein is coded for by gene 9 of the human type 1 (Wa) rotavirus. Gene 9 of type 1 human rotavirus has recently been cloned in *E. coli* and its sequence determined (Richardson, M. et al., J. Virol., 51, 860 (1984)).

Adenoviruses contain a linear duplex DNA molecule (m.w. $20 \times 10^6$–$25 \times 10^6$) that codes for 20–30 polypeptides. Many of these are incorporated into the viral particle which is morphologically complex and has a sophisticated assembly process. Previously SV40 T antigen has been expressed using an adenovirus recombinant (Solnick, D. Cell, 24, 135 (1981), Thummel, C. et at., Cell, 23, 825 (1981), Gluzman, Y. et al., in Eukaryotic viral Vectors, p. 187, Cold Spring Harbor (1982)). Also mouse dihydrofolate reductase has been expressed using an adenovirus recombinant (Berkner, K. and Sharp, P. A., Nucleic Acids Research, 12, 1925 (1984)).

Roy Curtiss III, in European Patent Publication 80,806 (1983) proposes a method for producing immunity to microbial diseases by the administration of a microbe containing a foreign gene which will express an antigen of a second microbe to which immunity is desired. He states that preferred oral preparations are enteric-coated. Dulbecco proposes recombinant adenovirus vaccines in which the surface protein of adenovirus is modified to contain in its structure a segment of foreign protein which will produce a desired biological response on administration to animals (PCT International Publication Number WO 83/02393 (1983)).

SUMMARY OF THE INVENTION

The invention sought to be patented in its method of treatment aspect comprises a method for producing antibodies or cell mediated immunity to an infectious organism in a warm-blooded animal which comprises orally administering to said warm-blooded animal, in an enteric coated dosage form, live recombinant adenoviruses in which the virion structural protein is unchanged from that in the native adenovirus from which the recombinant adenovirus is produced, and which contain the gene coding for the antigen corresponding to said antibodies or inducing said cell mediated immunity.

The invention sought to be patented in a subgeneric method of treatment aspect comprises a method for producing antibodies to hepatitis-B virus, rotavirus, or HIV in a warm-blooded animal which comprises orally administering to said warm-blooded animal live recombinant adenoviruses in which the virion structural protein is unchanged from that in the native adenovirus from which the recombinant adenovirus is produced, and which contain the gene coding for, respectively, a hepatitis-B antigen, a rotavirus antigen, or an HIV antigen.

The invention sought to be patented in its composition aspect comprises a vaccine for producing antibodies or cell mediated immunity to an infectious organism in warm-blooded animals comprising live recombinant adenoviruses in which the virion structural protein is unchanged from that in the native adenovirus from which the recombinant adenovirus is produced, and which contain the gene coding for the antigen corresponding to said antibodies or inducing said cell mediated immunity, said vaccine being formulated in an enteric coated dosage form.

The invention sought to be patented in a subgeneric composition aspect comprises a vaccine for producing antibodies to hepatitis-B virus, rotavirus, or HIV in warm-blooded animals, comprising live recombinant adenoviruses in which the virion structural protein is unchanged from that in the native adenovirus from which the recombinant adenovirus is produced, and which contain the gene coding for, respectively, a hepatitis-B antigen, a rotavirus antigen, or an HIV antigen, said vaccine being formulated in an enteric-coated dosage form.

DETAILED DESCRIPTION OF THE INVENTION

EXAMPLE 1

Adenovirus Vectors

Three adenovirus vectors (Gluzman, Y. et al., in Eukaryotic Viral Vectors p. 187, Cold Spring Harbor Laboratories, 1982) can easily be constructed. To maximize the length of foreign DNA that can be inserted, two expendable regions of the viral genome may be deleted, early regions 1 or early region 3 (E1 and E3), or both, of the adenovirus type 5 viral genome. ΔE1 is created by an in vivo recombinational event between a plasmid and a modified adenoviral DNA. (All plasmids described in this specification are propagated in *E. coli*). The plasmid is formed by insertion of adenoviral DNA sequences between 0 and 17 map units into pBR322 and subsequently, using restriction endonuclease digestion and ligation, deleting sequence between 1.4 and 9.1 map units and placing an XbaI restriction site at this junction. This plasmid is denoted in the art as pAC. The modified adenoviral DNA which contains a single XbaI restriction site at 4.0 map coordinates is formed as follows. XbaI cleaves wild type Ad5 DNA at four sites: 4, 29, 79, and 85 map. units. Modified DNA lacking sites at 29, 79, and 85 is isolated by cutting Ad5 DNA with XbaI, transfecting the DNA and isolating the modified adenovirus which lacks XbaI sites at positions 29 and/or 79. This procedure is repeated again and modified adenovirus is isolated containing only the XbaI site at position 4. Such modified adenoviruses can also be readily constructed using techniques of oligonucleotide-directed mutagenesis (Smith, M., and Gillam, S. (1981) in Genetic Engineering, Setlow, J. K. and Hollaender, A., Eds. Vol. 3, pp. 1-32, Plenum, New York). In this technique the XbaI restriction sites are destroyed using chemically synthesized oligonucleotides designed to produce silent changes in the amino acid coding regions defined by the respective XbaI restriction endonuclease sites. Vector ΔE3 is constructed by deletion of ΔE3 region sequences. Two modified adenoviruses (type 5) are formed by the procedures outlined above. One contains no XbaI sites, the other contains only the XbaI sites at map coordinates 29, 79, and 85. The left half of DNA of the mutant containing no XbaI sites is joined with the right half of DNA of the mutant containing XbaI sites at 79 and 85, forming a modified adenovirus containing XbaI sites at only 79 and 85 map coordinates. Cleavage of this DNA with XbaI followed by religation forms the ΔE3 viral DNA deleting the ΔE3 region between 79 and 85 map coordinates and placing a single XbaI cloning site at this junction. ΔE1 ΔE3 may be constructed by deletions in both regions in a similar manner.

In a fashion similar to construction of ΔE1, ΔE3, and ΔE1ΔE3 vectors of adenovirus type 5, vectors of adenovirus types 4 and 7 are formed. For example, in adenovirus type 7, the ΔE3 region is deleted between the XbaI site at 80.5 map coordinates and the EcoR1 site at map coordinate 85.

EXAMPLE 2

6X Series Plasmids (For $Hb_sA_g$ and rotavirus VP7)

Plasmids that allow the placement of the adenovirus 2 late promoter upstream from DNA coding for hepatitis B surface antigen or rotavirus VP7 followed by SV40 splicing signals may be constructed. Each of these is flanked by XbaI sites for insertion into the adenovirus ΔE1, ΔE3, or ΔE1ΔE3 vectors.

a. p6XH

Plasmid 6XH contains an XbaI linker at −400 bp of the Ad2 major late promoter and an Eco RI site at +33 bp, 8 bp before the end of the first adenovirus late leader. This is followed by an Eco RI linker at 26 bp preceding the ATG of $HB_sA_g$ followed by $HB_sA_g$ sequence of 678 bp to another Eco RI linker at 809 bp. This is followed by SV40 sequence extending from 2753–2516 bp on the SV40 map. These sequences are all inserted into the large pBR322 Bam HI to Eco RI fragment via XbaI linkers.

b. p6XR

Plasmid p6XR is made by joining the rotavirus VP7 gene with Eco RI linkers at nucleotide 6 and 1036 to the Ad2 major late promoter containing an XbaI site at −400 bp and an Eco RI linker at +331 and attaching SV40 sequences from 2753–2516 behind the VP7 gene with an Eco RI linker at 2753 (SV40 map coordinate) and an XbaI site at 2516 bp. This cassette is inserted into the large Eco RI to BamH fragment of pBR322.

c. Transfer of plasmid sequences to the viral DNA vector and production of recombinant adenovirus.

The transfer of the cassette of promoter-foreign gene-terminator to the adenovirus vector is done either as follows or by in vivo recombination (see detailed example below). The purified adenovirus vector DNA is cleaved with a restriction endonucleose followed by treatment with calf intestine alkaline phosphatase to prevent self ligation. Plasmid derived sequences are obtained by cleavage of p6XH or p6XR with XbaI. These are then ligated to the adenoviral vector DNA. Either 293 cells, (Graham, et al., Gen. Virol., 86 10 (1978)), Hela cells, or Wi-38 cells are then transfected with the ligation mixture and overlayed with agar. Plaques are picked 7–10 days later and viral stocks prepared.

EXAMPLE 3

Expression Assays

Three types of assays have been used to assess expression of hepatitis B surface antigen and rotavirus VP7. These are:

a. Indirect immunofluorescence.

Either mouse monoclonal antibodies or rabbit antisera are used to detect expression of recombinant ΔE1 and ΔE3 virus stocks containing $HB_sA_g$ or VP7 DNA sequences. Counterstaining is with goat anti-mouse or anti-rabbit FITC.

b. Immunoprecipitation.

Immunoprecipitation of $HB_sA_g$ or rotavirus VP7 in cells infected with the recombinant adenoviruses is done using either mouse monoclonal antibodies or rabbit polyclonal antisera against $HB_sA_g$ or rotavirus VP7 and protein A Sepharose CL4B.

c. RIA

Expression of $HB_sA_g$ is also tested by a commercially available radioimmunoassay (Ausria, Abbott Labs.).

EXAMPLE 4

Immunogenic Nature of the Recombinant Adenovirus

Live, lyophilized recombinant adenovirus contained in an enteric coated capsule is assessed for immunogenicity by administration ($10^4$–$10^5$ 50% infectious dose/tablet) to hamsters or chimpanzees and testing for antibody levels and protection from challenge.

The presently marketed adenovirus vaccine contains living lyophillized adenovirus of either type 4 or type 7 mixed with inert ingredients prepared in enteric coated tablets. Administration of tablets (approximately $10^4$ $TCID_{50}$ of virus) results in selective gastrointestinal infection without illness. The vaccine is safe; the induced infection is specifically restricted to the intestinal tract, and the vaccine virus is not transmitted from vaccinees to susceptible close contacts. Specific neutralizing antibody is noted in over 95% of vaccinated individuals 21 days after immunization. The new vaccines of the present invention which are specifically described are comprised of recombinant adenoviruses expressing hepatitis B surface antigen, LAV surface antigen, and rotavirus VP7 and are formulated and work in the same fashion as the present adenovirus vaccine except that antibody to hepatitis B surface antigen, LAV surface antigen or rotavirus VP7 is produced as well as antibody to adenovirus. In any of the embodiments of the invention, the administration of approximately $10^4$ $TCID_{50}$ of recombinant virus, or even considerably less, will, of course, produce the desired immunogenic response. The determination of the optimum dosage will vary depending on the particular recombinant adenovirus employed; determination of this optimum is within the skill of the art.

EXAMPLE 5

Detailed example of a recombinant that expresses authentic $HB_sA_g$

As a detailed example of the construction of one adenovirus recombinant, the $HB_sA_g$ gene of the adw subtype from 26 bp upstream of the $HB_sA_g$ translation initiation codon and 131 bp downstream from the translation termination codon was flanked by upstream sequences from the Ad2 major late promoter (+33 to 400 bp; Solnick, D., Cell, 24, 135–143 (1981) and by downstream sequences from SV40 (2753 to 2516 bp; Tooze, J. (Ed.) Molecular Biology of Tumor Viruses, Cold Spring Harbor Laboratory pp. 801–829 (1980)). This plasmid is termed p6XH (see above). These sequences were inserted into the unique XbaI site plasmid pAC that contains an insert of Ad5 DNA extending from the Eco RI linker at the left end of the adenovirus genome to the Hind III site at Ad5 map coordinate 17.0 (Gluzman, Y., Reichl, H., and Solnick, D., 1982, in (Y. Gluzman, Ed.) Eukaryotic Viral Vectors, Cold Spring Harbor Laboratories, p. 187–192). The new plasmids (pACH-2 and pACH-9) with the cassette containing the Ad2 major late promoter—$HB_sA_g$ gene—SV40 processing signals in either orientation, were cleaved with Hind III. The Hind III cleavage product of each was combined with the large XbaI fragment of the adenovirus mutant ΔE1 extending from map coordinates 9.1 to 100 (Gluzman, Y., Reichl, H., and Solnick, D., 1982 in (Y. Gluzman, ed.) Eukaryotic Viral Vectors, Cold Spring Harbor Laboratories, pp. 187–192). This DNA mixture was transfected (Graham, F. L. and ven der Eb, A. J. Virology 52, 456–467 (1973)) onto 293 cells (Graham, F. L., Smiley, J., Russell, W. C., and Nairn, R., J. Gen. Virol., 36, 59–72 (1977)) and cells were overlaid with agar for plaque detection. Approximately 10–14 days later, 54 plaques were picked and virus stocks generated from each. These viruses were screened for the presence of $HB_sA_g$ DNA by hybridization to a 32P-labeled $HB_sA_g$ DNA probe. Positive plaques (49 out of 54) were next infected onto monolayers of 293 cells and the expression of authentic $HB_sA_g$ was detected in cell lysates by both radioimmunoassay (AUSRIA, Abbott Laboratories, Inc. or NML-$HB_sA_g$ RIA, Nuclear-Medical Laboratories) and by immunoprecipitation of 35S-radiolabeled $HB_sA_g$ using a monoclonal antibody to $HB_sA_g$ (anti-a subtype, Boehringer Mannheim Biochemicals).

In the specific example above, we use the Ad2 major late promoter extending only 33 nucleotides downstream from the transcriptional initiation site so that the first splice site is not included. This promoter contains only the first part of the tripartite leader of the adenoviral major late promoter. However, the major late promoter from other adenoviruses particularly types 3, 4, 5, or 7 can be used and the full tripartite leader of this promoter can be used. In the following example we describe the construction of two bacterial plasmids, pHM1 and pHM2 which contain cassettes composed of the Ad2 major late promoter and the leftmost 168 bp of the 200 bp Ad2 tripartite leader followed by the $HB_sA_g$ gene and processing and polyadenylation signals from SV40 virus. These plasmids also contain adenovirus sequences flanking the cassette so that homologous recombination can be used to insert the cassette into the adenoviral genome. On the left the cassette is flanked by the leftmost 353 bp of the Ad5 genome-and on the right by map coordinates 8–15.5 of adenovirus 5. Plasmid pHM1 contains 19 bp of SV40 virus sequence (SV40 nucleotides 5173–5174) preceding the $HB_sA_g$ gene. Plasmid pHM2 is identical to pHM1 except that it does not contain this sequence.

The cassettes from both pHM1 and pHM2 were placed at the E1 region of the adenovirus 5 genome by the technique of homologous recombination as described above. Each plasmid was linearized and combined with the large XbaI fragment of the adenovirus mutant ΔE1 extending from map coordinates 9.1 to 100 (Gluzman, Y., Reichl, H. and Solnick, D., 1982 in (Y. Gluzman, ed.) Eukaryotic Viral Vectors, Cold Spring Harbor Laboratories, pp. 187–192). Plaques were picked and stock viruses generated from each.

When these stock viruses (HM1 and HM2) were infected on a human embryonic kidney (293) cell line (Graham, F. L., Smiley, J., Russell, W. C. and Nairn, R. (1977) J. Gen. Virol. 36, 59–72) we found, after 40 h infection, approximately 1 μg $HB_sA_g$ (based upon radioimmunoassay and comparison of cpm to NML-$HB_sA_g$ kit positive control) per 5×106 infected cells were observed in culture supernatants of HM2 infected cells. HM1 virus yielded approximately 60% of this amount. We found that the $HB_sA_g$ polypeptides produced by these viruses were glycosylated (P2) and non-glycosylated (P1) forms (Marion, P. L., Salazar, F. H., Alexander, J. J. and Robinson, W. (1979) J. Virol. 32, 796–802; Peterson D. L. (1981) J. Biol. Chem. 256, 6975–6983). At 40 h after infection most of the $HB_sA_g$ (78%) was secreted from cells into the culture medium as a particle (density=1.20 g/ml) the same or nearly the same as the 22 nm particle (Gerin, J. L., Purcell, R. H., Hoggan, M. D., Holland, P. V. and Chanock, R. M. (1969) J. Virol. 4, 763–768; Gerin, J. L., Holland, P. V., and Purcell, R. H. (1971) J. Virol. 7, 569–576) observed in human serum. HM2 yielded approximately 40% more $HB_sA_g$ than HM1. However, when HM2 was compared to the previously described hybrid adenovirus, ΔE1H, a 70-fold increase in $HB_sA_g$ polypeptide was noted by HM2 virus.

Instead of the adenoviral major late promoter, any other suitable eukaryotic promoter can be used, such as human metallothionein promoter or the human dihydrofolate reductase promoter. In addition, in our examples, we have used adenovirus type 5 DNA as vector for foreign gene expression; however, other adenovirus types can be used as vector, and particularly useful are types 3, 4, and 7 that are presently in use as vaccines.

Also, we describe the use of processing and polyadenylation signals from SV40 DNA; however, any suitable processing and polyadenylation signals may be used. These may come from adenoviral DNA, particularly types 3, 4, and 7.

EXAMPLE 6

Recombinant Adenovirus Ad7HZ6-1

Example of a recombinant adenovirus type 7, Ad7HZ6-1, that contains hepatitis B virus DNA inserted into the E3 region of the adenovirus genome and that replicates in human cells, directing the expression of hepatitis B virus surface antigen.

Ad7HZ6-1 was assembled by transfecting A549 cells (ATCC CCL 185) with overlapping viral DNA fragments that recombined in vivo to generate a complete recombinant viral genome capable of replicating and of producing infectious recombinant adenovirus (Davis, A. R., et al., [1985. Proc. Natl. Acad. Sci. USA 82, 7560–7564). The majority of the recombinant viral genome was derived from the Eco RI "A" genomic fragment of adenovirus type 7 (strain 55142) DNA that extends from map unit 0 to map unit 87. The other viral DNA fragment was a cloned, recombinant fragment that extends from map unit 68 to map unit 100 and contains the hepatitis B virus DNA; it was constructed as described below by standard techniques of molecular biology (Maniatis, T., et at., [1982. Molecular Cloning: A Laboratory Manual, Cold Spring Harbor Laboratory, Cold Spring Harbor, N.Y.).

Adenovirus type 7 (strain 55142) DNA was cloned into the Eco RI site of pBR322 (Pharmacia Inc., Piscataway, N.J.) as described (Hanahan, D. and Gluzman, Y. [1984] Molecular and Cellular Biology 4, 302–309). This procedure yielded recombinant plasmid WypAd7RIA-17 which contains adenovirus viral DNA between map unit 0 and map unit 87 with some deletions between map unit 40 and map unit 65. Recombinant plasmid WypAd7RIB-10 that contains the Eco RI "B" fragment which extends from map unit 87 to map unit 100 was also recovered. Portions of these two plasmids were combined to create a plasmid that contains adenovirus DNA between map unit 68 and map unit 100 except that the Hind III "H" fragment (map units 80–84) is replaced by a chemically synthesized polylinker region.

WypAd7RIA-17 was digested with Sal I and religated to make ChpAd717E27w.t. which lacks the Sal I "A" fragment (map units 18–68). ChpAd717E27w.t. was digested with Eco RV, Sal I and Hind III. Three of the resultant fragments, pBR322 between the Eco RV site and the Sal I site, adenovirus between map unit G8 (Sal I) and map unit 80 (Hind III), and the recombinant fragment containing adenovirus between map unit 84 (Hind III) and map unit 87 (Eco RI) joined to pBR322 from the Eco RI site to the Eco RI site, were separated by gel electrophoresis, purified and ligated together in the presence of a synthetic polylinker (Pharmacia Inc., Piscataway, N.J.) with Hind III ends and an internal Xba I site. The plasmid ChpAd717E27HΔ was recovered from this ligation and digested with Sal I and Eco RI to obtain a cloned adenoviral DNA fragment extending from map unit 68 to map unit 87, with the Hind III "H" fragment replaced by a synthetic polylinker.

The Eco RI site added to the terminus of the viral genome at map unit 100 during cloning was replaced by a Sal I site in the following steps. WypAd7RIB-10 was digested with Eco RI, the Eco RI sites were filled-in with Klenow DNA polymerase, Sal I linkers were ligated to the filled-in ends, followed by digestion with Sal I and Bam HI. The adenoviral DNA fragment extending from the Bam HI site at map unit 92.5 to the synthetic Sal I site at map unit 100 was cloned into pUC19 (Pharmacia Inc., Piscataway, N.J.). An adenoviral DNA fragment extending from map unit 87 (Eco RI) to map unit 92.5 (Bam HI) was prepared from WypAd7RIB-10 and added to this pUC19 recombinant to make ChpAd73'RS.1. ChpAd73'RS.1 was digested with Eco RI and Sal I to obtain a cloned adenoviral DNA fragment extending from map unit 87 (Eco RI) to map unit 100 (Sal I).

The cloned adenoviral DNA fragment extending from map unit 68 to map unit 87 obtained from ChpAd717E27HΔ and the cloned adenoviral DNA fragment extending from map unit 87 to map unit 100 obtained from ChpAd73'RS.1 were ligated together and then inserted into the Sal I site of pBR328 (Soberon, X., et al., [1980] Gene 9, 287–305) to create ChpAd7SalBHΔ.

Hepatitis B virus DNA was obtained from a plasmid that contains hepatitis B virus genome cloned at the Eco RI sites. The numbering of the nucleotides in this hepatitis B virus genome is identical to that of Ono et al., [1983] Nucleic Acids Res., 11, 1747–1757. The fragment of the hepatitis B virus genome that contains the genetic code for hepatitis B virus major surface antigen, the major envelope protein, lies between an FnuD II site at nucleotide 131 and a Hpa I site at nucleotide 966. This DNA fragment was excised by digestion with FnuD II and Hpa I, Sal I linkers were added, and it was cloned into a pBR322 derivative to create the plasmid, pHMHS.3C. Hepatitis B virus DNA clones are readily available, for example ATCC 45020 from the American Type Culture Collection.

The DNA fragment that contains the genetic code for the hepatitis B virus major surface antigen was obtained from pHMHS.3C by Sal I digestion, the terminii were filled-in with Klenow DNA polymerase and Nhe I linkers were added, followed by Nhe I digestion. This fragment was inserted into the unique Xba I site of ChpAd7SalBHΔ, between adenovirus map unit 80 and map unit 84, to create pCAd7ΔHS1-5. In pCAd7ΔHS1-5, the hepatitis DNA fragment that contains the genetic code for the hepatitis B virus major surface antigen is oriented so that the translation initiation codon is proximal to the putative adenovirus E3 region promoter. Digestion of the Cla I site in the pBR328 portion yielded linear pCAd7ΔHS1-5; this cloned, recombinant viral DNA fragment extending from map unit 68 to map unit 100 was cotransfected into A549 cells with the Eco RI "A" genomic DNA fragment to generate the novel recombinant adenovirus Ad7HZ6-1.

Within 8 to 14 days after transfection, recombinant viruses were recovered as plaques on the A549 cell sheet. These viruses were screened for their ability to direct the production of hepatitis B virus major surface antigen in infected A549 cells by radioimmunoassay (Organon Teknika Corp., Irving, Tex.). After several rounds of plaque purification, Ad7HZ6-1 was amplified to high liter and genomic DNA was prepared and mapped with restriction endonucleases. This analysis confirmed the expected structure. A549 cells infected with Ad7HZ6-1 secreted approximately 1 μg of immunoreactive hepatitis B virus major surface antigen per 5 million cells within 48 hours (this corresponded to approximately 40,000 cpm per 100 μl sample of tissue culture supernatant using the radioimmunoassay). Ad7HZ6-1 has been deposited with the American Type Culture Collection and has been designated ATCC VR2167.

EXAMPLE 7

Recombinant Adenovirus Ad7HZ2–28

Ad7HZ2–28 was isolated after transfection of A549 cells with two overlapping Ad7 DNA fragments that recombined in transfected cells and produced a complete, infectious recombinant adenovirus. The two DNA fragments contributing to the recombination were (1) the EcoRI A fragment derived from genomic DNA map units 0 to 87; and (2) a cloned DNA fragment that extends from map units 68 to 100 and contains the hepatitis B virus surface antigen gene. The construction of the plasmid, pWyAd7E3HSB-C, for the second fragment is described below using standard techniques in molecular biology as summarized in (molecular cloning: A Laboratory Manual, Maniatis, T., et at. (1982) Cold Spring Harbor Laboratory, Cold Spring Harbor, N.Y.).

Adenovirus type 7 (strain 55142) ATCC VR2183 DNA fragment from map unit 68 to 87 was cloned in pBR322 after digestion with SalI and EcoRI to give the plasmid pWyAd768-87. Adenovirus DNA fragment from map unit 87 to 100 was cloned in pBR322 as described (Hananan D., and Gluzman, Y. (1984). Molec. and Cell. Biol. 4:302–309), to give the plasmid pWyAd7BN-10. In pWyAd7BN-10 an EcoRI site was added at map unit 100. pWyAd768-87 and pWyAd7BN-10 were used to construct pAd768-100 which contains Ad7 DNA extending from map 68 to 100 cloned as EcoRI to SalI fragment in pUC18.

In order to insert hepatitis B virus DNA that contains the gene for hepatitis B virus surface antigen into the E3 region, a fragment from pWyAd768-100 extending from map units 78.5 to 80.2 was isolated after SacII and NheI digestion. This fragment was cloned in a pBR322 derivative pBR322H–/S+. pBR322H–/S+ was prepared from pBR322 by HindIII digestion, fill-in of the HindIII site using Klenow DNA polymerase, addition of SAcII linkers, SAcII digestion and ligation. The fragment isolated from pWyAd768-100 (map units 78.5 to 80.2) was cloned into NheI and SacII digested pBR322H/S+ to yield the plasmid pBAd7Y2-7.

Hepatitis B virus DNA was obtained from a plasmid that contains the hepatitis B virus genome cloned at the Eco RI site. The numbering of the nucleotides in this hepatitis B virus genome is identical to that of Ono, et al. [1983] Nucleic Acids Res. 11. 1747–1757. The fragment of the hepatitis B virus genome that contains the genetic code for hepatitis B virus major surface antigen, the major envelope protein, lies between an FnuD II site at nucleotide 131 and a Hpa I site at nucleotide 966. This DNA fragment was excised by digestion with FnuD II and Hpa I, SalI linkers were added, and it was cloned into a pBR322 derivative to create the plasmid, pHMHS.3C. Hepatitis B virus clones are readily available, for example ATCC 45020 from the American Type Culture Collection.

The DNA fragment that contains the genetic code for the hepatitis B virus major surface antigen was obtained from pHMHS.3C by SalI digestion, the terminii were filled-in with Klenow DNA polymerase, HindIII linkers were added followed by HindIII digestion. This fragment was cloned into the unique HindIII site of pBAd7Y2-7 at adenovirus map unit 80, to create pBAd7YHS2–9. In pBAd7YHS2–9, the hepatitis B virus surface antigen gene is oriented so that the translation initiation codon is proximal to the adenovirus E3 promoter.

pBAd7YHS2–9 was digested with SacII and NheI and the adenovirus sequences from map unit 78.5 to 80.2 were joined to the large fragment of pWyAd768-100 that was also prepared by SacII and NheI digestion. This final plasmid construct, designated pWyAd7E3HSB-C contains adenovirus sequences from map units 68 to 100 and has the hepatitis B virus surface antigen gene sequence in the E3 region at map unit 80.

PvuI digestion at sites within the pUC18 portion of the plasmid gave linear pWyAd7E3HSB-C which was cotransfected into A549 cells with the adenovirus 7 EcoRI A fragment to generate the novel recombinant adenovirus Ad7HZ2-28.

Plaque purified Ad7HZ2-28 and A549 cells were examined for the production of hepatitis B virus surface antigen by radioimmunoassay (Organon Teknika Corp., Irving, Tex.).

Approximately 32,000 cpm per 100 μl sample of tissue culture media was found to be secreted within 48 hours postinfection. This corresponds to approximately 1 μg of HBSAg per 5 million cells. Preparation of genomic DNA from infected cells and analysis of the genomic recombinant DNA confirmed the structure as expected.

EXAMPLE 8

Recombinant Adenovirus Ad4HHXHS

Example of a recombinant adenovirus type 4, Ad4HH×HS, that contains the hepatitis B virus surface antigen gene with a synthetic splice acceptor sequence, which was inserted into the E3 region of adenovirus 4.

The recombinant adenovirus, Ad4HH×HS, contains 28 bp of middle surface antigen gene, 12 bp Ad5 hexon splice acceptor and the hepatitis B surface antigen gene inserted into the HpaI site of the E3 region of Ad4. The construction of Ad4HH×HS involved four steps:

1. subcloning of hepatitis B surface antigen gene.
2. cloning of the E3 region to the right-hand terminal region of Ad4.
3. subcloning of hexon splice acceptor and hepatitis B surface antigen.
4. generation of recombinant viruses by homologous recombination in vivo and identification of virus.

The hepatitis B virus major surface antigen gene (major envelope gene) was obtained from a plasmid, which contains HBV genome cloned at the Eco RI site. The numbering of the nucleotides in this HBV genome is identical to that of Ono et at., 11983] Nucleic Acids Res. 11, 1747–1757. Xho 1 linkers were added at the FnuDII site (nt. 131 ) and NheI linkers were added at the HpaI site (nt. 966). The fragment was subcloned at a constructed XhoI and NheI sites in a pBR322 derivative. The plasmid called pMPHSHpNh. The plasmid, Ad4E3, 71–100, contains the 29 mu fragment of Ad4 which extends from the HindIII site (71 mu) to the right-hand terminal end. The right-hand end of Ad4 was cloned by NaOH treatment followed by the addition of EcoRI linkers as described by Berkner and Sharp, (Nucl. Acids Res. 11, 6003 [1983]). The EcoRI C fragment (83 mu–100 mu) was cloned into pBR322. The XhoI EcoRI fragment (996.1–100mu) was subcloned into the pUC18 vector at the SalI and EcoRI sites. Ad4 DNA was prepared from Ad4 virus amplified in W138 cells. The HindIII to SalI fragment (71 mu–99.6mu) isolated from Ad4 viral DNA was subcloned into the pUC18, 96–100 plasmid at the SalI of Ad4 (99.6mu) and the HindIII site of pUC18 vector, resulting in the plasmid called pAd4E3, 71–100.

The plasmid, pAd4E3, 71–100, was modified in the following way so that the hepatitis surface antigen gene could be inserted at the HpaI site (76.3 map unit). In one isolate, Spe I linkers were added to the HpaI site. In a second isolate, the linkers below, called HHx, were added to the HpaI site and the plasmid digested with SalI:

5'ATTGCCTCTCACATCTCGTCAATCTC-CGCCGCCAGAG 3'

3'TAACGGAGAGTGTAGAGCAGTTAGAG-GCGGCGGTCTCAGCT 5'

The HBV surface antigen gene was inserted at the HpaI site by ligation of (a) the HBV XhoI to Nhe I fragment (nt. 131–966), (b) an Ad4 fragment from the 71 mu to 76.3 mu containing the HHx linker at 76.3 mu, i.e. the HindIII to SalI fragment and (c) Ad4-pUC18 fragment (76.3 mu–100 mu) from the SpeI site (76.3 mu) to the HindIII site of pUC18.

The recombinant adenovirus, Ad4E3HH×HS, was generated by cotransfection of 10 μg pAd4HpSpHS and 5 μg BclA fragment of Ad4 (0–87 mu) into A549 cells as described (Berkner and Sharp, [1983], Nucl. Acids Res. 11, 6003). Plaques were picked into 2 ml media, and 1 ml was amplified on A549 cells. The supernatants were screened for the secretion of HBV surface antigen by a radioimmunoassay (Organon Technika Corp., Irving, Tex.). The recombinant adenovirus, Ad4HH×HS, produces significant quantities of Hepatitis B surface antigen. Ad4HH×HS has been deposited with the American Type Culture Collection and has been designated ATCC VR 2210.

EXAMPLE 9

Recombinant Adenoviruses WyAd7H 6 and WyAd7H 7

Cloned DNA of the adenovirus type 7 strain 55142, was engineered by introducing an Xba I site at 159 base pairs from the right hand end of the adenovirus genome in the following manner. The EcoRI B fragment from adenovirus type 7 was cloned into pBR322, the plasmid was partially digested with Rsa 1 and Xba I linkers were ligated to the viral DNA. The resultant clones were screened and those with unique Xba I sites were selected and sequenced to assure that no deletions had occurred.

In order to express the major hepatitis B surface antigen ($HB_sA_g$), it was necessary to introduce the major late promoter sequence and three pan leader sequence that is found on all adenovirus mRNAs. The major late promoter sequence was isolated by digesting with Xho I and Pvu II and subcloning the adenovirus DNA fragment from 5,643 to 5,934 base pairs. The three part leader sequence was selected from cDNA clones of adenovirus mRNA. The promoter sequence included from the Pvu II site at 5,934 base pairs to the Taq I site at 9,530 base pairs, where a SalI linked was added, with the intron sequences being deleted from the cDNA clones. The polyadenylation site consisted of the SV40 polyA site which included the fragment between the Bcl I site and BamH I sites from 2,770 base pairs to 2,533 base pairs of the SV40 genome. All three fragments (promoter, leader and polyA site) were introduced into the plasmid which contained the adenovirus EcoRI B fragment to produce the expression vector (pAd7BMTS-2).

Hepatitis B virus DNA was obtained from a plasmid that contains the hepatitis B virus genome cloned at the Eco RI site. The numbering of the nucleotides in this hepatitis B virus genome is identical to that of Ono, et al. [1983. Nucleic Acids Res. 11, 1747–1757. The fragment of the hepatitis B virus genome that contains the genetic code for hepatitis B virus major surface antigen, the major envelope protein, lies between an FnuD II site at nucleotide 131 and Hpa I site at nucleotide 966. This DNA fragment was excised by digestion with FnuD II and Hpa I, Sal I linkers were added, and it was cloned into a pBR322 derivative to create the plasmid, pHMHS.3C. Hepatitis B virus clones are readily available, for example ATCC 45020 from the American Type Culture Collection.

The HBSAg gene was removed from a plasmid (pHMHS.3C) by digesting with Sal I and ligated into the expression vector. The resultant plasmids (pAd7BMTHS-15 and pAd7BMTHS-26), which contained either one copy or two copies, respectively, of the $HB_sA_g$ gene, were ligated to the EcoRI A fragment of adenovirus type 7 and transfected into A549 cells. Plaques were obtained, amplified on A549 cells and tested for the expression of $HB_sA_g$. Clones which were positive for surface antigen expression were passed again in A549 cells to make virus stocks and were also grown in W138 coils. The DNA of viruses WyAd7H 6 and WyAd7H 7, containing one copy or two copies of the $HB_sA_g$ gene, were analyzed by restriction mapping and electrophoresis in agarose gels and were found to be non-defective and did not contain any deletions in the viral DNA.

EXAMPLE 10

Recombinant Adenoviruses WyAd7ChH1–16 and WyAd7ChH2–8

A different expression cassette was developed by Chiron and was introduced into the plasmid which contained the adenovirus type 7 EcoRI B fragment with a unique XbaI site at 159 bp from the right hand end of the genome. Adenovirus DNA (from plasmid WyAdR1A-17) fragment XhoI (nucleotide 5643) to the HindIII site was cloned into pBR327. The tripartite leader was designed based on the published adenovirus type 7 sequence from the PvuII site (nucleotide 5934) within the first leader segment through the end of the first segment (nucleotide 5944), containing the second leader segment (nucleotide 6962–7033), and the third leader segment (nucleotide 9477–9563) and ending with a Hind III site. The poly A site for the hexon gene of adenovirus type 7, the major late promoter and the tripartite leader were cloned into the plasmid which contained viral DNA with a unique XbaI site near the inverted terminal repeat. The DNA constructions contained the promoter oriented in either the left hand orientation or the right hand orientation. The HBSAg gene was obtained from the pHMH5.3C plasmid as described in Example 9 and was cloned into the plasmid listed above.

The plasmids were ligated to the EcoRI A fragment and transfected into A549 cells. The plaques of virus that were obtained contained the surface antigen gene and the promoter sequence in a left-hand orientation (WyAd7ChH 1–16) or the right-hand orientation (WyAd7ChH 2–8). Both constructions expressed $HB_sA_g$ and were nondefective.

EXAMPLE 11

Recombinant Adenovirus WyAd7IHH-I

The intron between the first and second part of the tripartite leader sequence was isolated from the adenovirus type 7 genome by digesting the adenovirus DNA with XhoI and purifying the fragment from agarose gels (5,643 to 8,168 base pairs on the adenovirus genome). The fragment was inserted by digestion with XbaI and ligation into a cassette which contained the major late promoter, the tripartite leader sequence and the SV40 poly A site. The leader sequence was joined by digestion with ScaI and ligation. The intron was further modified by treatment with BssHII which removed a fragment that corresponded to between 6,178 and 6,517 base pairs on the adenovirus genome DNA. The entire cassette was inserted into the XbaI site that had been constructed at 159 base pairs from the right-hand end of the adenovirus genome. The major $HB_sA_g$ gene was obtained from pHMHS.3C as described in Example 9 and inserted into the SalI site. The hexon polyA site was substituted for the SV40 polyA site by digesting the plasmids with SpeI and exchanging fragments between pAd7ChHI-1 and pAd7ChHA-6 (left-hand orientation) as well as pAd7IChH3-10 and pAd7ChHB-31 (right-hand orientation). The SpeI sites were found near the right-hand end of the adenovirus genome and in the $HB_sA_g$ gene. The plasmids were also treated with StuI and HindIII linkers were added to the blunt ends by ligation. After digestion with HindIII another fragment was removed from the intron which corresponded to between 6,135 and 6,819 base pairs of the adenovirus genome.

An additional modification was made to the clone which contained the major late promoter in the left-hand orientation.

A fragment of DNA which contained the adenovirus type 7 BamHI fragment that spanned from 70 map units to 90 map units of the adenovirus genome was cloned into the expression vector after digestion with BamHI. This fragment was obtained from the plasmid ChpAd7SalIBHΔ, and it contained a deletion in the E3 region that was made by the removal of a HindIII fragment from map units 80 to 84. The plasmid (pAd7ΔBH1–11) was subsequently digested with BglI to linearize the DNA and cotransfected with the adenovirus type 7 EcoRIA fragment into A549 cells. The plaque that was obtained after 21 days was amplified in A549 cells and the virus recombinant, WyAd7IHH-1, was positive for the expression of hepatitis B surface antigen.

EXAMPLE 12

Recombinant Adenovirus Ad4iHR

Recombinant virus Ad4iHR has a cassette for production of $HB_sA_g$ positioned at a SalI site found in Ad4 138 bp from the extreme right-hand terminus. The cassette contains (1) the Ad4 major late promoter (MLP), (2) followed by the first leader of the Ad4 tripartite leader CFPL), (3) followed by the first intron of the tripartite leader (TL), followed by (4) the second two exons of the Ad4 TPL, followed by (5) the $HB_sA_g$ gene, followed by (6) a processing and polyadenylation signal from SV40 virus. It was prepared and positioned in the rightward orientation at the unique SalI site as follows: Ad4 is known to have an XhoI site at 15.9 map units (Ginsberg, E. [ed], 1984, The Adenoviruses, Plenum Press, N.Y.), and it was determined by restriction enzyme mapping to have a ScaI site at 19.7 map units. DNA fragment 1 (approx. 1300 bp) from XhoI to ScaI contains the Ad4 major late promoter, the first leader of the TPL and the entire intron between the first and second exon of this TPL and one-half of the second exon.

DNA fragment 2 from this ScaI to a TaqI site 100 bp downstream of this ScaI site in Ad4 was obtained from a cDNA clone of the Ad4 TPL and was determined by DNA sequencing to contain the second-half of the second exon and two-thirds of the third exon for the TPL. This cDNA clone was obtained by standard methods (Maniatis, T. et al [1985], Molecular Cloning: A Laboratory, Cold Spring Harbor, N.Y.) with the use of the oligonucleotide 5'TCTF-CAAGGGGGAACCCG3' as probe. Use of the oligonucleotide was based upon the published sequence in this region (exon 2 of the TPL in Ad7 DNA found in (Ginsberg et al. 1984 ibid)). In DNA fragment 2, this TagI site was converted to a SalI site by treatment with Klenow DNA polymerase 1 and ligation of a SalI linker. DNA fragment 3, the $HB_sA_g$ gene, was obtained from pHMHS.3C by SalI digestion inserted into the SalI site of pBR328 (Soberon, X., et at. [1980], Gene 9, 287–305) to create ChpAd7SalBHΔ.

Hepatitis B virus DNA was obtained from a plasmid that contains the hepatitis B virus genome cloned at the Eco RI site. The numbering of the nucleotides in this hepatitis B virus genome is identical to that of Ono, et al [1983] Nucleic Acids Res. –, 1747–1757. The fragment of the hepatitis B virus genome that contains the genetic code for hepatitis B virus major surface antigen, the major envelope protein, lies between an FnuD II site at nucleotide 131 and a Hpa I site at nucleotide 966. This DNA fragment was excised by digestion with FnuD II and Hpa I, Sal I linkers were added, and it was cloned into a pBR322 derivative to create the plasmid, pHMHS.3C. DNA fragment 4 was the SV40 processing and polyadenylation signal, extending from 2753–2516 bp on the SV40 map (Tooze, I. [ed]), 1980 DNA Tumor Viruses, Cold Spring Harbor Laboratory, N.Y.) with a SalI site at 2,753 bp and a XhoI site at 2,516 pb.

Fragments 1 (XhoI-ScaI), 2 (ScaI-SalI), 3 (SalI-SalI) and 4 (SalI-XhoI) were assembled using standard manipulations (Maniatis, T. et al., 1982, ibid) in bacterial plasmid pBR322 (Bolivar et at. [19771, Gene 2.95) modified to contain an XhoI site at the junction of the BamHi (375 bp from the EcoRI site) and PvuII site (2,067 bp from the EcoRI site in BR322). Then the entire cassette was cloned (as an XhoI fragment) in either orientation at the unique SalI site of pAd4R1C-25. This plasmid contains the rightmost EcoRI fragment of Ad4 (Ad4EcoRIC) cloned at the EcoRI site of a pBR322 modified such that the SalI site (650 bp from the EcoRI site) is destroyed.

The Ad4EcoRI C fragment, prepared from Ad4 DNA, strain CL68578, was cloned by treatment of purified Ad4 DNA with NaOH to remove terminal protein complex followed by re-annealing, ligation of EcoRI linkers, and treatment with EcoRI as described in detail (Hanahan, D. and Gluzman, Y. [19843 Molecular and Cellular Biology 4, 302–309). The final plasmid, termed pAd4CMT(i)H-45 contained the above cassette cloned at the SalI site in the rightward orientation. Virus Ad4iHR was formed by co-transfection of the BclIA fragment of Ad4 DNA with pAd4CMT(i)H45 cloned with EcoRI. When A549 cells were infected with Ad4iHR, $HB_sA_g$ activity was demonstrated using a commercial radioimmunoassay (Organon Technika Corp., Irving, Tex.).

EXAMPLE 13

Recombinant Adenoviruses Ad4(di)HR and Ad4(di)HL

Recombinant virus Ad4diHL and Ad4diHR were made in the same fashion as Ad4iHR except that the 1,000 bp intron between TPL exon 1 and TPL exon 2 was trimmed by deleting 500 bp from a StyI site approx. 500 bp from the 5' XhoI site to a SacII site approx. 1,000 bp from the 5' XhoI site. In addition, both orientations of this DNA fragment (rightward and leftward) were used. When Ad549 cells were infected with suspensions of Ad4(di)HR and Ad4(di)HL, $HB_sA_g$ activity was demonstrated in both cases.

EXAMPLE 14

Recombinant Adenoviruses Ad4XiHR, Ad4X(di)HR

Recombinant viruses Ad4XiHR and Ad4X(di)HR were made in exactly the same fashion as Ad4iHR and Ad4(di)HR except that a synthetic 112 bp Ad4 hexon processing and polyadenylation signal on a SalI to XhoI DNA fragment replaced the SV40 polyadenylation signal. The DNA sequence used for this signal was determined by DNA sequence analysis of the published sequence of the Ad2 hexon polyA site (LeMoullec, J. M. et al [1983], J. Virol. 48: 127) and DNA sequence analysis of the corresponding region in Ad4. By comparing the two sequences, one was able to determine which elements appear to be necessary for function. When A549 cells were infected with a plaque suspension of Ad4XiHR and Ad4X(di)HR, $HB_sA_g$ activity was demonstrated in both instances.

EXAMPLE 15

Recombinant Antivirus WyAd7LAV# 17

This is an example of a recombinant adenovirus type 7, WyAd7LAV#17, that contains lymphadenopathy associated virus DNA within an expression cassette inserted between the E4 region and the right ITR of the adenovirus genome and that replicates in human cells, directing the expression of LAV envelope protein.

WyAdLAV#17 is similar to WyAd7H#6 and many of the plasmids used to construct WyAd7H#6 were also used to construct WyAd7LAV# 17. WyAd7LAV#17 was assembled in vitro by ligating together the Eco RI "A" genomic fragment of adenovirus type 7 (strain 55142) DNA and a cloned, recombinant derivative of the adenovirus type 7 Eco RI "B" fragment that contains the LAV DNA inserted into a genetically engineered expression cassette driven by a copy of the adenovirus type 7 major late promoter. The ligated viral DNA was transfected into A549 cells (ATCC CCL 185) from which recombinant virus was subsequently recovered (Davis, A. R., et at., [1985] Proc. Natl. Acad. Sc. USA 82, 7560-7564).

A description of the procedures used to clone adenovirus type 7 DNA and to construct the expression cassette is given in Example 9. Standard techniques of molecular biology were utilized to create a recombinant plasmid, pAd7BMTS-2, that contains the Eco RI "B" fragment extending from map unit 87 to a synthetic Eco RI site at map unit 100. An expression cassette containing the adenovirus major late promoter followed by a cDNA copy of the tripartite leader, a synthetic SalI site and the SV40 early polyadenylation signal was inserted into a synthetic Xba I site at map unit 99.6 The major late promoter within the expression cassette was oriented in the same direction as the endogenous major late promoter at map unit 16, and transcription should proceed toward map unit 100. Cloned DNA fragments which encode vital antigens can be inserted at the synthetic SalI site within the cassette and can be expressed during the course of virus infection.

Lymphadenopathy associated virus DNA was subcloned from a subgenomic clone of LAV inserted into the SacI site of pUC18, pUC18LAV, (Wain-Hobson, [1985] Cell 40, 9–17). A549 cells infected with WyAd7LAV#17 express immunologically reactive LAV envelope protein. This LAV antigen can be detected by cytoimmunofluorescence staining using either mouse monoclonal antibody directed against the gp 120K portion of the LAV envelope protein (Biotech Research Labs, Rockville, Md.) or human polyclonal antibodies from patients with AIDS ! (Cellular Products Inc., Buffalo, N.Y.). Electrophoretic analysis of metabolically radiolabeled LAV envelope protein that was immunoprecipitated by monoclonal antibody from A549 cells infected with WyAd7LAV#17 indicates that the LAV envelope protein is of the expected molecular weight, approximately 120 Kilodaltons, and that it is secreted into the media. WyAd76AV#17 has been filed with the American Type Culture Collection and has been designated ATCC VR 2185.

EXAMPLE 16

Recombinant Adenoviruses AD5 HBsAg78.5 and Ad5 HBsAG E3

Adenovirus type S (Ad5) (ATCC VR-5) was cloned into the Bam HI site of the bacterial plasmid pBR322 (Pharmacia Inc., catalog 27-4902-01) as described (Berkner, K. L., and Sharp, P. A., Nucleic Acids Res. 11, 6003 [1983]) except that Bam HI linkers (GGGATCCC, Pharmacia Inc.) were used instead of Eco RI linkers. The resulting plasmid, p60W-43, was modified by excision of the Xba 1 fragment between adenovirus map unit (MU) 78.5 and MU 84.7 from p60W-43 grown in a Dem *E. coli* strain (NEB208, available from New England Biolabs). The Xba 1 fragment was separated from the modified plasmid, p60W E3 by electrophoresis in a low melting agarose gel and the modified plasmid was recovered, ligated, and propagated in *E. coli* (general techniques of the art are described in Maniatis, T., Fritsch, E. F., Sambrook, J., [1982J Molecular Cloning: A Laboratory Manual, Cold Spring Harbor Laboratory, Cold Spring Harbor, N.Y.). These recombinant adenovirus plasmids, p60W-43 and p60W E3–6, are prepared for insertion of heterologous DNA by digesting plasmid DNA grown in a Dam$^+$ strain of *E. coli* (New England Biolabs) with Xba 1 and treating the digested DNA with alkaline phosphatase.

The hepatitis B virus (HBV), ADW strain, major surface antigen coding sequence (HS) was excised from the recombinant plasmid pHM1–11 (Davis, A. R., et alia, Proc. Natl. Acad. Sci. USA 82, 7560 [1985]; another plasmid which includes HS is freely available, ATCC 45020, Moriarty et alia, Proc. Natl. Acad. Sci. USA 78, 2606 [1981] with SalI. The overhanging ends were filled in with Klenow polymerase, the HS was purified from a low temperature agarose electrophoresis gel and Nhe 1 linkers (CGCTAGCG, Pharmacia) were ligated to HS, followed by digestion with Nhe 1 and a second round of gel purification to yield pure HS fragment with overhanging Nhe 1 linkers.

The HS with overhanging Nhe 1 linkers was ligated to each of the prepared recombinant plasmids, p60W-43 and p60W E3-6, to construct the recombinant plasmids p60WHBsAgII-3 and p60W E3HBsAgII-12. These plasmids were digested with BamHI and transfected into the 293 cell line (ATCC CRL 1573), together with the Eco RI "A" fragment of genomic Ad5 DNA which extends from Mu 0 to Mu 76, as described (Davis, A. R., et alia, ibid). Homologous recombination occurs in vivo between the adenovirus DNA segments common to both the genomic DNA fragment and the cloned DNA fragment, Mu 60 to Mu 76, to generate full length recombinant viruses recovered as plaques on the 293 cell sheet (Stow, N. D. J. Virol. 37, 171 [19811]). Recombinant viruses were screened for their ability to direct the production of HBV major surface antigen (S) in infected 293 cells by radioimmunoassay (Organon Teknika Corp., Irving, Tex.; Abbott Laboratories, N. Chicago, Ill.). Recombinant viruses which scored positive for S production were plaque purified, amplified to high titer, further purified by isopycnic centrifugation and the viral DNA was isolated as described (Davis, A. R., et alia, ibid). Analysis of vital DNA confirmed the expected structures. HS is inserted downstream of the E3 region promoter, within the second E3 intron, approximately 100 base pairs (bp) downstream of the Y leader (FIG. I) (Cladaras, C., et alia, Virol.140, 28 [1985]; Cladaras, C., et alia, ibid., p44).

In the recombinant Ad5 HBsAg78.5, no Ad5 DNA is deleted and the HS is approximately 150 pb upstream of the initiation codon for the vital glycoprotein gp 19K. In the recombinant Ad5HBsAG E3, the Mu 78.5 to Mu 84.7 Xba 1 "D" fragment is replaced by HS. WyAd5 HBsAg E3 has been deposited with the American Type Culture Collection and has been designated ATCC VR 2211.

Both recombinants are nondefective and can be propagated in a cell line appropriate for pharmaceutical use, W138 (ATCC CCL 75) as well as the transformed cell line, A549 (ATCC CCL 185) or the adenovirus transformed cell line, 293 (ATCC CRL 1573). Cells infected with 10 plaque forming units of either recombinant virus per cell should secrete at least 1 $g of immunoreactive S into the medium per 5 million cells within 48 hr. S secreted by these viruses is of the correct molecular weights corresponding to both unglycosylated and glycosylated protein (Heermann, K. H., et alia, J. Virol. 52, 396 [1984]) as determined by electrophoretic analysis of immunoprecipitated proteins (Mason, B. B., et alia, J. Virol. 33, 1111 [1980]).

Recombinant adenoviruses with similar structures can be constructed by using these same techniques applied to Adenovirus type 4 (ATCC VR-4) and Adenovirus type 7 (ATCC VR-7). ATCC catalog numbers refer to the American Type Culture Collection, Catalogue of Cell Lines and Catalogue of Animal Viruses, Rockville, Md.

EXAMPLE 17

Recombinant Adenovirus WyAd7IHH-3

Adenovirus vector was further modified by the addition of an EcoRI site at 80 map units. This site was produced by digesting with StuI and the ligation of EcoRI linkers. After digesting with EcoRI and religation, a fragment of adenovirus DNA was deleted which was from 84 to 87 map units.

The resultant plasmid, pAd7AHEH-3, was transfected into A549 cells and plaques were isolated which expressed HB$_S$A$_g$ (Ad71HH-3). An analysis of the viral DNA from these recombinants confirmed that a deletion existed in the adenovirus DNA between 80 and 87 map units. WyAd7IHH-3 has been deposited with the American Type Culture Collection, and has been designated ATCC VR 2221.

EXAMPLE 18

Recombinant Adenoviruses WyAd7IHENV-4, 11, and 42

Constructs which contained the envelope gene from the AIDS virus were made by removing the HBsAg gene from other cassettes (pAd7 HEH-3, pAd7HRHL-5 and pAd7IHH-11) by digestion with SalI and ligation with the LAV-ENV gene which had been purified from pUCLenv.8. The envelope gene was the same as was used in the preparation of WyAd7LAV#17.

After isolation of the envelope gene, the DNA fragment was ligated into a plasmid which contained the adenovirus expression cassette with an intron and either a 1.6 or 2.6 kilobase deletion in the E3 region (80-84 map units and 80-87 map units respectively). Plasmids called pAd7IHENV-4 and pAd7IHENV-42 contained the expression cassette in either the right or left hand orientation, respectively, and a 2.6 KB deletion. The plasmid denoted pAd7IHENV-11 contained the expression cassette in the right-hand orientation and a 1.6 kilobase deletion. These three plasmids were linearized with BglI and transfected into A549 along with the adenovirus EcoRI "A" fragment. After 2-3 weeks, plaques were picked and amplified on A549 cells. The presence of the envelope gene was confirmed by performing a Hirt extraction on infected cells and an analyzing restriction enzyme digest on agarose gels.

The viruses were named according to which plasmid they originated from (WyAd7IHENV-4, 11 and 42). The production of the AIDS envelope antigen was determined by immunoprecipitation with a monoclonal which reacted with gp120/160. The identity of the precipitated protein was further confirmed by analysis on polyacrylamide gels. WyAd7IHENV-4 and WyAd7IHENV-42 have been deposited with the American Type Culture Collection and have been designated ATCC VR 2222 and ATCC VR 2220, respectively.

EXAMPLE 19

Recombinant Adenovirus WyAd7IHART-4

WyAd7IHART-4 was isolated by transfecting A549 cells with two overlapping DNA fragments that recombined in vivo to generate a complete recombinant vital genome capable of replicating and producing infectious recombinant adenovirus (Davis, A. R. et al. [1985] Proc. Natl. Acad. Sci. 82, 7560–7564). The two DNA fragments used for recombination were (1) the EcoRI "A" fragment derived from adenovirus type 7 genomic DNA that extends from map units (m.u.) 0 to 87 and (2) a cloned Ad7 DNA fragment that extends from m.u. 70 to 100 and contains REV(ART/TRS) gene. The construction of the plasmid, WyAd7 BH1–11.ART-4 for the second fragment is described below using standard techniques in molecular biology as summarized in (molecular cloning: A Laboratory Manual, Maniaties, T., et al. (1982) Cold Spring Harbor Laboratory, Cold Spring Harbor, N.Y.).

REV(ART/TRS) gene which was constructed as described below was inserted in the expression cassette WyAd7BH1–11 that contains the HBsAg between the E4 region and the inverted terminal repeat (ITR). HBsAg was removed by SalI digestion and the ART gene was inserted at the SalI site to generate the plasmid WyAd7 BH1–11.ART-4.

The expression cassette consisted of the adenovirus major late promoter (MLP), the tripartite leader sequence (TPL) and the hexon polyadenylation site. The major late promoter within the expression cassette was oriented in the same direction as the endogenous major late promoter at map unit 16, and transcription should proceed toward map unit 100.

The construction of REV(ART/TRS) involved the following steps: ART gene consists of two exons. The first part of the entire exon containing a SacI-HindIII-SalI linker in front of ATG codon of ART gene and a part of the second exon up to AvaI site (Position 7950 on LAV genome; Wain-Hobson, (1985) Cell 40, 9–17) was synthesized chemically. The rest portion of the second exon including the termination codon was derived from AvaI (7950)-XhoI (8454) fragment of puc18 Lenv.8, a subgenomic clone of lymphadenopathy associated virus (LAV). These two fragments were then ligated to pTZ18R at the SacI-SalI site to generate a plasmid called pTZ18R.ART-3. This plasmid was then digested with HindIII and the HindIII fragment containing the ART gene was then cloned in pUC19 at the HindIII site. One of the resultant plasmids designated as pUC19.ART.d3–15 was digested with SalI and the SalI fragment containing the ART gene was isolated. This fragment was then inserted into the synthetic SalI site within the expression cassette.

Approximately (11–18) days after transfection, the recombinant adenovirus was recovered as plaques on the A549 cell sheet. Following plaque purification, WyAd71HART-4 DNA was extracted by Hirt's extraction procedure and then analyzed with restriction endonucleases. This analysis confirmed the expected structure. The effect of ART gene on the HIV envelope was then analyzed by infecting A549 cells with both WyAd71HART-4 and WyAd71HENV-42 viruses. WyAd71HENV-42 contains HIV env gene in the terminal cassette and has been described in Example 18. The total cell lysate was prepared at different time points (24, 30, 48, and 72 hr.) and the amount of HIV envelope gene was measured by antigen capture/ELISA assay. Approximately 50–70 fold increased envelope gene production was observed in the presence of ART gene. Electrophoretic analysis of metabolically radiolabeled cells infected with both viruses indicate the presence of gp160 and gp120, the products of HIV envelope gene. gp41 was also detected by using western blot analysis with inactivated human sera from AIDS patients. Immunoprecipitation with monoclonal antibody also confirmed the presence of gp160 and gp120. WyAd71 HART-4 has been deposited with the American Type Culture Collection and has been designated ATCC VR 2226.

EXAMPLE 20

Recombinant Adenovirus WyAd71HART-5,ENV-42

Recombinant adenovirus type 7, WyAd71HART-5.ENV-42 that contains REV(ART/TRS) gene in the deleted (80–87 m.u.) E3 region and ENV gene in the cassette that was inserted between the E4 and ITR region was isolated by transfecting A549 cells with two overlapping DNA fragments that recombined in vivo to generate a complete recombinant viral genome capable of replicating and producing infectious recombinant adenovirus. The two DNA fragments used for recombination were (1) The EcoRI "A" fragment derived from adenovirus type 7 genomic DNA that extends from map units (m.u.) 0 to 87 and (2) a cloned DNA fragment that extends from 70 to 100 m.u. which contains both REV and ENV gene. The construction of the plasmid, WyAd71HART-5.ENV-42 is described below. The plasmid pAd7 HEH-3 which contains HBsAg in the terminal cassette was digested with SalI to remove HBsAg and then ligated to (SalI-XhoI) fragment obtained from pUCLenv.8 which contained the HIV ENV gene to generate the plasmid, WyAd71HENV-42. The plasmid pAd7 HEH-3 contains 80–87 m.u. E3 deletion with a EcoRI site in it. The plasmid, WyAd71HENV.42 was then digested with EcoRI and then ligated to EcoRI fragments of ART gene which was derived from plasmid, pTZ18RART4.R1 which contains the ART gene flanked by EcoRI restriction sites.

Approximately (11–18) days after transfection, the recombinant adenovirus was obtained as plaques on A549 cell sheet. Following plaque purification, the recombinant adenoviruses were analyzed by restriction enzymes on Hirt extract DNA. Most of the plaques had deletion except one which had the expected structure. This plaque has been purified 2 times and a couple of plaques were analyzed on random basis by Hirt DNA analysis and by ELISA during each plaque purification. All of them had the expected structure and produced large amount of HIV ENV antigen WyAd71HART-5.ENV-42 has been deposited with the American Type Culture Collection, and has been designated ATCC VR 2241.

In practicing the method of this invention, where the foreign gene is inserted in deleted early region 3 of the adenovirus, the recombinant virus remains infective, and the vaccination requires nothing more than delivery of the recombinant virus to the gut. On the other hand, early region 1 is essential to adenovirus infectivity. Therefore, if the foreign gene is inserted in deleted early region 1, helper virus must be co-administered. This helper virus is conveniently unmodified, infectious adenovirus. Also, the helper virus can itself be a defective virus with a deletion which can be complemented by the recombinant virus. In this fashion virus growth and foreign antigen production would be elicited only in cells infected with both viruses. This defective helper virus can be of the same or of different subtype as the recombinant virus. If of differing subtype (e.g. if recombinant virus was Ad4 subtype and the defective virus of Ad7 subtype), formation of wild type virus through recombination should be minimized. Propagation of virus for vaccine production can be accomplished either through co-cultivation of both viruses in human diploid fibroblasts or cultivation of viruses separately in cell lines known to complement each of the defects.

In addition to the E 1 and E3 regions, there are several other regions of the viral genome where the cassette containing promoter, tripartite leader, foreign gene, and processing and polyadenylation signals may be inserted. These include a region between Ela and Elb, regions at the left and right ends of the genome, and at the E4 region, and between L5 and E4 regions. Some examples are given below:

Ad5 contains an Eta promoter at map coordinate 1.4 and an Elb promoter at map coordinate 4.7. The polyadenylation site for Ela is at map coordinate 4.6, nucleotide 1631, at nucleotide 1671 is the TATA box for the Elb promoter. At nucleotide 1572 there is a unique HpaI site (GTTAAC). This site can be utilized for placement of the adenovirus type 2 major late promoter and hepatitis B surface antigen and use of the Ela polyadenylation site. Polyadenylation of Ela can be provided by placement of a polyadenylation signal from SV40 viral DNA behind Eta or from the L4 region of the virus. The additional DNA in the genome in the above construct may be compensated by removal of DNA determined non-essential in the E3 region.

Other insertion points are the extreme left and right ends of the genome. At the left end the position will be between the 116 bp inverted terminal repeat and the TATA box of the E4 promoter. In Ad2 there is an Mbo II site at 99.3 map units. This is 191 bp from the extreme right end of the viral DNA. In Ad5 there is a ThaI (FnU4DII) site 240 bp from the left end of the genome. This region is between the ITR and upstream of the E4 TATA box. Again, if necessary, insertion will be made into an E3 deletion mutant to accommodate the extra DNA.

In each case these same regions can be used as insertion points for the cassette of the adenovirus major late promoter, adenovirus tripartite leader, foreign gene and processing and polyadenylation signals in adenovirus type 4 and type 7 strains that are used for the presently marketed adenovirus vaccines.

Although this specification specifically refers to adenovirus of types 4, 5, or 7, live, infectious adenovirus of any type may be employed in this invention. Adenovirus of types 4 or 7 are preferred since these are the types presently employed in commercial adenovirus vaccines. Similarly, although specific reference has been made to vaccines producing antibodies to hepatitis-B, rotavirus, and HIV, our invention provides oral vaccines against any infectious agent containing an antigen to which a warm-blooded animal will produce antibodies or cell mediated immunity, and which antigen is coded for by a gene composed of up to about 3000 base pairs. Thus, for example, included within the scope of the invention are immunization against such diseases as influenza, parainfluenza, respiratory synctial virus disease, hepatitis A, acquired immunodeficiency syndrome (AIDS), cholera, E. coli, pertussis, diphtheria, tetanus, shigellosis, gonorrhea, mycoplasma pneumonia, and so on.

EXAMPLE 21

Recombinant Adenovirus WyAd7ΔE3 r80–88)TPL-S-35: (WyAd7delE3H)

This is an example of a recombinant adenovirus type 7, that contains synthetic WyAd7 cDNA copy of TPL and HBsAg DNA inserted within endogenous E3 mRNAs having a large deletion and produces high level of HBsAg protein mediated by the internal TPL sequences positioned immediately upstream to HBsAg gene. The E3 region protein coding sequences downstream to the HBsAg insertion site has been completely deleted in this recombinant. The recombinant virus isolation was carried out by recombining in vivo two overlapping WyAd7 DNA fragments transfected into A549 cells (Berkner, K. L. and Sharp, P., Nucleic Acids Res. 11:6003, 1983; and Davis, A. R., et at., Proc. Natl. Acad. Sci. USA, 82:7560, 1985). One of the DNA fragments was purified from WyAd7 vaccine strain (55142) as EcoRI A fragment spanning map units 0–87 portion of the viral genome. The second fragment was ClaI digested recombinant plasmid pAd7 SalIB (ΔE3 80–88) TPL-S-35. This contains a DNA segment of synthetic WyAd7 TPL appended to HBsAg gene and WyAd7 DNA between m.u. 68 to 100 as SalIB fragment, but without most of the E3 region sequences between m.u. 80–88. The construction of this recombinant plasmid involved the standard molecular cloning techniques (Molecular Cloning: A Laboratory Manual, Eds. Maniatis, T., et al. [1982] Cold Spring Harbor Laboratory, Cold Spring Harbor, N.Y.) and the details are as follows:

(a) Construction of WyAd7 TPL and HBsAg coding gene. A pBR327 derivative plasmid pAd7ChHA2–3 contained HBsAg coding DNA fragment between nucleotides 131 and 966 (Ono, et al., Nucleic Acids Res. 11:1747) as synthetic SalI fragment that was cloned into the synthetic SalI site located immediately downstream to the end of the synthetic cDNA copy of WyAd7 TPL-third leader. By site directed mutagenesis, a restriction site NheI was introduced immediately upstream to the 5' end of TPL and just downstream to the stop codon of HBsAg gene at nt 840 and resulted in plasmid pAd7ChHA2-318R-8 that was renamed as pAd7NCTPLH18R-7, from which the TPLHBsAg sequences can be isolated as NheI-NheI DNA fragment.

(b) Generation of a plasmid with large deletion (m.u. 80–88) in E3 Region of WyAd7: From a pBR328 vector plasmid that contained WyAd7 SalI B DNA (m.u. 68-m.u. 100) fragment with the 80–84 m.u. deletion in E3 region a derivative was constructed. This was called pAd7SalIB (68–100)ΔE3 (80–84)-12, in which the HindIII, BamHI, NheI sites of pBR328 were deleted. Then the Ad7 E3 region sequence between the StuI site present in a linker at 80 m.u. and the ApaLI site (located upstream to Ad7 E3B polyadenylation signal) at ~88 m.u. was deleted to yield pAd7SalIB (68–100)ΔE3 (80–88)-78.

(c) Generation of Ad7-TPL-HBsAg-recombinant plasmid: The Ad7TPL-HBsAg containing DNA fragment was isolated as NheI/NheI fragment from above-mentioned pAd7NCTPLH 18R-7, and cloned into the synthetic XbaI site present at 80 m.u. in pAd7SalIB (68–100)ΔE3 (80–88) -78 to yield pAd7SalIBΔE3 (80–88)-TP-S-35. This plasmid contained TPL-HBsAg sequence at 80 m.u. in E3 region and provided the rest of Ad7 genome with 80–88 m.u. deletion for the generation of recombinant virus that produced high level of HBsAg protein as detected by radioimmuno assay using AUSRIA test kit of Abbot Labs.

WyAd7ΔE3 (80–88) TPL-S-35 (WyAd7delE3H) was deposited with the American Type Culture Collection and has been designated ATCC VR2295.

EXAMPLE 22

Recombinant Adenovirus WyAd4(3.11)ΔE3TPLH (WyAd4delE3H)

The recombinant virus construction strategy is similar to that in example 21, except that the WyAd4 synthetic TPL was appended to HBsAg gene and placed within a 3.11 kilo base pair deletion in E3 region of Ad4 genome. The steps involved in the construction are as follows:

(a) Construction of Ad4TPL-HBsAg containing plasmid: A synthetic cDNA copy of WyAd4 TPL containing DNA was isolated as a SmaI-EcoRI fragment and cloned into SmaI-EcoRI sites of pTZ18R (Pharmacia) vector to yield a plasmid pAd4TPL-MLP18R-12. By site directed mutagenesis, NheI and SalI sites were created at 5' and 3' ends of Ad4TPL sequences respectively to generate pAd4TPL-18R-21. The Ad4 TPL containing NheI-SalI DNA fragment was isolated from pAd4TPL-18R-21 and subcloned into NheI-SalI polylinker sites of pTZ18RD, to obtain pAd4TPL18RD-38 The HBsAg coding DNA fragment was isolated from pAd7NH18R-2, that was derived from pAd7ChHA2–3 mentioned under Example 21, Section (a). The HBsAg coding sequence was inserted downstream to Ad4TPL sequence present in pAd4TPL-18RD38 to yield pAd4TPLH. 18RD-47.

(b) Generation of Ad4-TPL-HBsAg recombinant plasmid: The Ad4TPL-HBsAg sequence containing DNA in pAd4.TPLH.18RD-47 was isolated as XbaI-NheI fragment and inserted at the synthetic SpeI site located within the 3.11 kb deletion (between 77 m.u. –86 m.u.) present in Ad4E3 region clone pAd4SDΔE3.8.12. The resulting recombinant plasmid clone which also contained the rest of Ad4 genome between m.u. 71 to m.u. 100, is called pAd4SDΔE3TPLH 142–423.

(c) Isolation of recombinant virus: The Ad4TPL-HBsAg containing recombinant plasmid pAd4SDΔE3TPLH142–423 was linearized with EcoRI and transfected into A549 cells along with the purified Ad4 BclI A fragment containing 0–87 map units of WyAd4 genome. The overlapping region recombination between the above mentioned two DNA fragments yielded the recombinant WyAd4(3.11 )ΔE3TPLH, producing abundant quantities of HBsAg protein as detected by radioimmuno assay using AUSRIA kit of Abbott Labs. The recombinant has been renamed as WyAd4delE3H.

WyAd4(3.11)ΔE3TPLH (WyAd4delE3H) was deposited with the American Type Culture Collection and bears the designation ATCC VR2303.

EXAMPLE 23

Recombinant Adenovirus WyAd7H

Ad7-HBsAg recombinant with complete E3 region: The recombinant contains the HBsAg and regulatory sequences inserted at the 3' end non-coding E3B region and retains all the E3 protein coding region as they are in vaccine strain WyAd7. The construction of this recombinant involved the following steps:

(a) Creating a new site of insertion at 3' non-coding part of E3B region: A synthetic SpeI linder/adapter was inserted at the BspMI site located between Ad7E3 region last openreading frame stop codon and the E3B polyadenylation signal sequence in a subclone of E3b/L5 region and called pGEM3Zf(+) (Ad7E3BSpeI). The sequence of Ad7E3B region it contains is between SacI (~88 m.u.) and HpaI (~90 m.u.) that was subcloned into pGEM3Zf(+) vector from a plasmid containing m.u. 60–m.u. 100 of WyAd7DNA. The SpeI linker/adapter also provides stop condons in all the three reading frames and duplicates 10 bp of E3B sequences on either side of SpeI site to retain possible E3B polyadenylation functions.

(b) Source of HBsAg sequence and the regulatory elements as a cassette: The cassette containing-XbaI site, BamHI site, synthetic Ad7 hexon related splice acceptor, hexon leader, HBsAg coding sequence, SalI site, Ad7 hexon polyadenylation signal sequence and XbaI site was isolated as a DNA fragment with XbaI sites at both of the ends from a parent plasmid, pAd7SHLHPAΔX-7. The internal XbaI site within the HBsAg coding sequence was removed by site-directed mutagenesis of plasmid pAd7SAH×HPA-18R-10, while the coding amino acid remained unaltered. The pAd7SAH×HPA-18R-10 plasmid was assembled in pTZ18R vector, to contain synthetic Ad7 hexon like splice acceptor, hexon leader, HBsAg coding region and Ad7 synthetic hexon polyadenylation signal sequences, that were obtained from pAd7SAH×TPLH-50 and pAd7TPLHBsAg-52. In these plasmids the HBsAg (adw) coding sequence was originated from pAd7TP-HS-11, wherein a SalI site was added immediately downstream to stop codon of HBsAg open reading frame. The prior source of adw type HBsAg sequence and synthetic Ad7 hexon polyadenylation signal sequences were from pAd7HEH18R-153-4, while it was a derivative of pAd7NCTPLH 18R-7.

(c) Insertion of HBsAg sequence as a cassette into the new site at 3' non-coding part of E3B region: The cassette containing Ad7 hexon related splice acceptor, hexon leader, HBsAg and hexon polyadenylation signal sequence with XbaI sites at both of the ends was isolated from the plasmid pAd7SHLHPAΔX-7 (described above, Section -b). It was cloned into the synthetic SpeI site of pGEM3Zf(+) (Ad7E3BSpeI) and yielded the plasmid p3Zf(+) (Ad7E3B-xsa-xl-S-xpa)T3. From this plasmid, the SacIHincII DNA fragment containing E3B region (~88 and ~90 m.u.) and the HBsAg cassette sequences was cloned into SacI-HpaI sites (~88 and ~90 m.u.) of a plasmid[Ad7(84–100)]5a6, that contained Ad7 genome between map units 84 and 100. The resulting recombinant plasmid was called p18R [Ad7 (84100)E3B-S]-G14. The pUC18R[Ad7(84-100)]5a6 was a derivative of pAd7SalIB(68–100) clone, that contains WyAd7 genome from 68 m.u. to 100 m.u. in pUC18R vector.

(d) Generation of recombinant virus: The recombinant plasmid p18R [Ad7 (84100)E3B-S]G14 was digested with BglI enzyme and co-transfected with agarose gel purified WyAd7 EcoRI A fragment of 0–87 m.u. The recombinant virus isolated produced high levels of HBsAg protein as tested by radioimmuno assay using AUSRIA test kit of Abbott Labs. The recombinant has been named WyAd7H.

EXAMPLE 24

Recombinant Adenovirus WyAd4H

This is an example of Ad4-HBsAg recombinant with complete E3 region.

The recombinant contains the TPL-HBsAg sequences inserted at the 3' end non-coding E3B region as in WyAd7H (Example 23) and retains all the E3 protein coding region as they are in vaccine strain WyAd4. The construction of this recombinant involved the following steps:

(a) Creating a new site of insertion at 3' non-coding part of Ad4E3B region: A synthetic linker/adapter with NheI and XbaI sites at 5' end and SpeI at 3' end was inserted into the SpeI site created between the stop codon of last E3 region protein (14.7K) open reading frame and the E3 B polyadenylation signal sequences in a subclone called pAd4 (86.7–91.5/SpeI)-65. The SpeI site that is located immediately downstream to Ad4 14.7K stop codon was created by site-directed mutagenesis of plasmid pAd4 (86.7–91.5). This in turn was obtained by subcloning the SacI (86.7 m.u.)-SphI (91.5 m.u.) DNA fragment of Ad4E3B region into pTZ19R. The SacVSphI fragment was isolated from the plasmid pAd4MPRIC-25 that contains EcoRI-C fragment (m.u. 83–m.u. 100) of WyAd4 MP vaccine strain that was cloned into pBR322 vector.

Once the linder/adapter NheI-XbaI-SpeI was inserted into the SpeI site in plasmid pAd4 (86.7–91.5/SpeI)-65, it generated two cloning sites namely XbaI at 5' end of the linker followed by E3B repeated synthetic sequences and the SpeI site at the 3' end of the linker. This new plasmid was called p19R(Ad4E3B)326-A4.

(b) Construction of Ad4TPL-HBsAg cassette containing plasmid-pAdTPLHx-SHpA-10: The cassette containing NheI site, Ad4TPL, Ad4 hexon leader, SalI site, HBsAg, SalI site, XbaI site, Ad4 hexon polyadenylation signal and NheI site has been put together by several steps of subcloning into pTZ18RD vector. In summary (i) the NheI site, Ad4TPL, Ad4 hexon leader—were obtained by plasmids namely pAd4TPLA HBsAg-64 (derived from pAd4TPLH- 18RD-47, pAd4TPL- 18RD-38, and pAd7NH- 18R-2) and pAd4TPLHxL-5. (ii) The HBsAg sequence was obtained from pAdSTPLS-8 and pAd7TPL-HS-HpA-52 (derived from pAd7TPLHS-11 and pAd7HEH18R-153-4). The HBsAg sequence was edited such that SalI site is created immediately upstream to AUG start codon and another SalI site is brought immediately downstream to TAA stop codon of HBsAg. (iii) The Ad4 hexon polyadenylation signal was obtained from pAd4TPLHxL-S-HpA- 13, 15 (derivative of Ad4TPL-S-HpA-42, and pAd4TPLHpA-38).

(c) Insertion of TPL-HBsAg sequence as a cassette into the new SpeI site at 3' noncoding part of E3B region: The cassette containing NheI site, Ad4TPL, Ad4 hexon leader, SalI site, HBsAg, SalI site, XbaI site, Ad4 hexon polyadenylation signal and Nhei site was isolated from the plasmid mentioned above -pAd4TPLHx-S-HpA-10. The cassette was isolated as NheI/NheI DNA fragment by gel purification and inserted into the new SpeI site present in p18R (Ad4E3B)326A4. The resulting Ad4E3BHBsAg recombinant plasmid is called p18R(Ad4E3B-TPL xl-S-xpA)32812.

(d) Generation of Ad4-TPL-HBsAg recombinant plasmid: The TPL-HBsAg cassette within Ad4E3B region fragment SacI and SphI was purified as BclI (87.1 m.u.)cassette-BclI (~87.4 m.u.)DNA fragment from the above plasmid p18R (Ad4E3B-TPL-xl-S-xpA)32812. This fragment was cloned into the BclI (~87.1 m.u./BclI (~87.4 m.u.) sites of large plasmid pAd4 (71–100) 25.4 that contained HindIII (m.u. ~71) - EcoRI (m.u. 100) fragment of WyAd4 vaccine strain. The resulting recombinant large plasmid is called pAd4 (77-100) TPL-S-412G1.

(e) Isolation of recombinant virus: The recombinant plasmid pAd4 [(77–100) TPL-xl-S-xpA]412G1 was digested with HindIII enzyme and co-transfected into A549 cells along with agarose gel purified Ad4 viral DNA (BclI A fragment) containing 0–87 map units of WyAd4 genome. The overlapping homologous region recombination between the transfected two DNA fragments yielded the viral plaques. These were amplified, plaque purified and identified by Hirt DNA analysis for the expected structure. As predicted they also produced abundant quantities of HBsAg protein as detected by radioimmuno assay using AUSRIA kit of Abbott labs. The recombinant has been named WyAd4H.

EXAMPLE 25

Ad7-eny$_{MN}$

The construction of recombinant adenoviruses containing the coding sequence of the env (gp 160) gene of MN strain of HIV-1 is described briefly as follows: The 125 bp (6243 to 6367) fragment of the amino (NH$_2$) terminus of the env (gp160) gene including the initiation codon (ATG) as well as consensus Kozak sequence was amplified by polymerase chain reaction (PCR) from the clone pMNST 1-8-9. This fragment was then cloned in pGEM vector and the resultant clone was designated as pGEMMNenv. The following fragments of DNA were isolated by digesting with the restriction enzymes KpnI and XbaI from the clone PAd5tpl$_{MN}$env 223 (6367 bp to 8816 bp), XhoI+KpnI fragment from PGEMenv and salI+XbaI fragment from pAd7tpl 18RD. All of these fragments were ligated together and the resultant clone was designated as pAd7tpl$_{MN}$env. This plasmid was then digested with XbaI and treated with calf intestine alkaline phosphatase (CIAP). The NheI+XbaI fragment of Hrev gene was then isolated from the plasmid, pAd7tplHrev 18RD. The clone that was obtained after ligating these two fragments together was designated as pAD7tpl$_{MN}$envtplHrev. This plasmid was then digested with NheI+XbaI and then ligated to the E3 deletion plasmid of Ad7, pAd7ΔE3 (68 m.u. to 100 m.u. deletion) that was also digested with XbaI and then treated with CIAP. The resultant plasmid was designated as pAD7ΔE3tpl$_{MN}$envtpl$_{MN}$Hrev. This plasmid was digested with EcoRI and mixed with the EcoRI (0–87 m.u.) fragment of the Ad7 genomic DNA. A549 cells were then transfected with these DNAs. Recombinant plaques obtained from in vivo recombination were identified by the appropriate restriction digestion analyses of the Hirt DNA. The plaques were also identified by the production of gp160, gp120, and gp41 using appropriate antibodies on Western blots.

EXAMPLE 26

Ad4-env$_{MN}$ and Ad5-eny$_{MN}$

The construction of Ad4 and Ad5 recombinants are the same as that of Ad7-env$_{MN}$ except that for Ad4, EcoRI digested DNA from pAd4ΔE3tpl$_{MN}$envtplHrev was combined with the BclI (0–87 m.u.) fragment from the Ad4 genomic DNA to produce the recombinant Ad4 virus. Similarly for Ad5, MluI-digested DNA from pAd5ΔE3tpl$_{MN}$envtplHrev was combined with the SpeI (0–75 m.u.) fragment of Ad5 genomic DNA to produce the recombinant Ad5 adenovirus. Like Ad7, both Ad4 and Ad5 recombinants were obtained from A549 cells.

Measurement of Replication and Antigen Expression

Human A549 cells were infected (MOI 10:1 ) with recombinant adenovirus types 4, 5, and 7 that contained either the LAV or MN env genes. At 34 hours post-infection, virus titer and env antigen expression was determined in duplicate samples. One dish of infected cells was subjected to 3 cycles of freeze thawing and the cell lysate was tested for the presence of infectious virus by plaque assay. The second culture dish was washed, detergent solubilized, and an aliquot of the cell lysate was loaded on to a 10% polyacrylamide gel. Following electrophoresis, the separated proteins were transferred to nitrocellulose by a Western blot apparatus. The transferred proteins were immunostained with anti-env reagents. A known standard, recombinant gp160, was added prior to electrophoresis. The resulting immunoblot was scanned by a densitometer and the amount of recombinant env determined. There were no significant differences seen between wild type adenoviruses and the recombinant adenoviruses expressing either the LAV or MN env gene. Both types of recombinant adenoviruses, LAV or MN, produced similar amounts of env antigen. Therefore, both types of Ad-env recombinants, LAV and MN, were able to grow in human A549 cells as well as their corresponding wild type adenovirus, and were able to express recombinant env antigen. These results therefore demonstrate that both the LAV and MN adenovirus recombinants are capable of generating cell mediated, humoral, and secretory immunity in a mammal. The data obtained are summarized in the table below.

ADENOVIRUS REPLICATION AND ANTIGEN EXPRESSION

| Adenovirus | pfu/cell × $10^2$ | μg env/$10^6$ cells |
| --- | --- | --- |
| Ad4 wild type | 5.4 | 0 |
| Ad4-env | 9.1 | 2.1 |
| Ad4-env$_{MN}$ | 6.8 | 2.7 |
| Ad5 wild type | 22 | 0 |
| Ad5-env | 86 | 5.4 |
| Ad5-env$_{MN}$ | 18 | 5.7 |
| Ad7 wild type | 18 | 0 |
| Ad7-env | 11 | 3.1 |
| Ad7-env$_{MN}$ | 7.8 | 3.6 |

What is claimed is:

1. A method for producing antibodies or cell mediated immunity to Hepatitis-B virus in a warm-blooded animal which comprises orally administering to said warm-blooded animal, in an enteric coated dosage form, live recombinant adenoviruses in which the virion structural protein is unchanged from that in the native adenovirus from which the recombinant adenovirus is produced, and which contain the gene coding for the hepatitis-B surface antigen which corresponds to said antibodies or induces said cell mediated immunity.

2. A method according to claim 1 wherein said live recombinant adenovirus is adenovirus type 4 or 7 with the gene coding for the hepatitis-B surface antigen located in deleted early region 3.

3. A method according to claim 1 wherein the recombinant adenovirus is WyAd7ΔE3 (80–88) TPL-S-35.

4. A method according to claim 1 wherein the recombinant adenovirus is WyAd4(3.11)ΔE3TPLH.

5. A method according to claim 1 wherein the recombinant adenovirus is WyAd7H.

6. A method according to claim 1 wherein the recombinant adenovirus is WyAd4H.

7. A method according to claim 1 wherein the recombinant adenovirus is WyAd7H 6.

8. A method according to claim 1 wherein the recombinant adenovirus is WyAd7H7.

9. A method according to claim 1 wherein the recombinant adenovirus is WyAd7ChH 1–16.

10. A method according to claim 1 wherein the recombinant adenovirus is WyAd7ChH 2–8.

11. A method according to claim 1 wherein the recombinant adenovirus is WyAd7IHH-1.

12. A method according to claim 1 wherein the recombinant adenovirus is Ad4iHR.

13. A method according to claim 1 wherein the recombinant adenovirus is Ad4diHL.

14. A method according to claim 1 wherein the recombinant adenovirus is AD5 HBsAg78.5.

15. A method according to claim 1 wherein the recombinant adenovirus is Ad5 HBsAG E3.

16. A method according to claim 1 wherein the recombinant adenovirus is WyAd7IHH-3.

17. A method according to claim 1 wherein the recombinant adenovirus is WyAd7ΔE3 (80–88) TPL-S-35 (WyAd7delE3H).

18. A method according to claim 1 wherein the recombinant adenovirus is WyAd4(3.11)ΔE3TPLH (WyAd4delE3H).

19. A method for producing antibodies or cell mediated immunity to adenovirus and Hepatitis-B virus in a warm-blooded animal which comprises orally administering to said warm-blooded animal, in an enteric coated dosage form, live recombinant adenoviruses in which the virion structural protein is unchanged from that in the native adenovirus from which the recombinant adenovirus is produced, and which contain the gene ceding for the Hepatitis-B surface antigen which corresponds to the antibodies or cell mediated immunity to the Hepatitis B virus.

20. A method according to claim 19 wherein said live recombinant adenovirus is adenovirus type 4 or 7 with the gene coding for the hepatitis-B surface antigen located in deleted early region 3.

21. A method according to claim 19 wherein the recombinant adenovirus is WyAd7ΔE3 (80–88) TPL-S-35.

22. A method according to claim 19 wherein the recombinant adenovirus is WyAd4(3.11)ΔE3TPLH.

23. A method according to claim 19 wherein the recombinant adenovirus is WyAd7H.

24. A method according to claim 19 wherein the recombinant adenovirus is WyAd4H.

25. A method according to claim 19 wherein the recombinant adenovirus is WyAd7H 6.

26. A method according to claim 19 wherein the recombinant adenovirus is WyAd7H 7.

27. A method according to claim 19 wherein the recombinant adenovirus is WyAd7ChH 1–16.

28. A method according to claim 19 wherein the recombinant adenovirus is WyAd7ChH 2–8.

29. A method according to claim 19 wherein the recombinant adenovirus is WyAd7IHH-1.

30. A method according to claim 19 wherein the recombinant adenovirus is Ad4iHR.

31. A method according to claim 19 wherein the recombinant adenovirus is Ad4diHL.

32. A method according to claim 19 wherein the recombinant adenovirus is AD5 HBsAg78.5.

33. A method according to claim 19 wherein the recombinant adenovirus is Ad5 HBsAG E3.

34. A method according to claim 19 wherein the recombinant adenovirus is WyAd7IHH-3.

35. A method according to claim 19 wherein the recombinant adenovirus is WyAd7ΔE3 (80–88) TPL-S-35 (WyAd7delE3H).

36. A method according to claim 19 wherein the recombinant adenovirus is WyAd4(3.11)ΔE3TPLH (WyAd4delE3H).

37. A vaccine for producing antibodies or cell mediated immunity to Hepatitis-B virus in warm-blooded animals comprising live recombinant adenoviruses in which the virion structural protein is unchanged from that in the native adenovirus from which the recombinant adenovirus is produced, and which contain the gene coding for the hepatitis-B surface antigen which corresponds to said antibodies or induces said cell mediated immunity, said vaccine being formulated in an enteric coated dosage form.

38. A vaccine according to claim 37 wherein said live recombinant adenovirus is adenovirus type 4 or 7 with the gene located in deleted early region 3.

39. A vaccine according to claim 37 wherein the recombinant adenovirus is WyAd7ΔE3 (80–88) TPL-S-35.

40. A vaccine according to claim 37 wherein the recombinant adenovirus is WyAd4(3.11)ΔE3TPLH.

41. A vaccine according to claim 37 wherein the recombinant adenovirus is WyAd7H.

42. A vaccine according to claim 37 wherein the recombinant adenovirus is WyAd4H.

43. A vaccine according to claim 37 wherein the recombinant adenovirus is WyAd7H 6.

44. A vaccine according to claim 37 wherein the recombinant adenovirus is WyAd7H 7.

45. A vaccine according to claim 37 wherein the recombinant adenovirus is WyAd7ChH 1–16.

46. A vaccine according to claim 37 wherein the recombinant adenovirus is WyAd7ChH 2–8.

47. A vaccine according to claim 37 wherein the recombinant adenovirus is WyAd7IHH-1.

48. A vaccine according to claim 37 wherein the recombinant adenovirus is Ad4iHR.

49. A vaccine according to claim 37 wherein the recombinant adenovirus is Ad4diHL.

50. A vaccine according to claim 37 wherein the recombinant adenovirus is AD5 HBsAg78.5.

51. A vaccine according to claim 37 wherein the recombinant adenovirus is Ad5 HBsAG E3.

52. A vaccine according to claim 37 wherein the recombinant adenovirus is WyAd7IHH-3.

53. A vaccine according to claim 37 wherein the recombinant adenovirus is WyAd7ΔE3 (80–88) TPL-S-35 (WyAd7delE3H).

54. A vaccine according to claim 37 wherein the recombinant adenovirus is WyAd4(3.11)ΔE3TPLH (WyAd4delE3H).

* * * * *